United States Patent [19]

Steuri

[11] Patent Number: 4,636,329

[45] Date of Patent: Jan. 13, 1987

[54] SHAMPOO COMPOSITIONS COMPRISING QUATERNARY IMIDAZOLINIUM COMPOUND AND ALKYLAMIDO BETAINE HAVING LOW PH RANGE

[75] Inventor: Christian Steuri, Fairfield, Ohio

[73] Assignee: The Procter & Gamble Company, Cincinnati, Ohio

[21] Appl. No.: 818,994

[22] Filed: Jan. 13, 1986

Related U.S. Application Data

[63] Continuation of Ser. No. 735,709, May 17, 1985, abandoned, which is a continuation of Ser. No. 506,917, Jun. 22, 1983, abandoned.

[51] Int. Cl.$^4$ .................... A61K 7/06; C11D 3/26; C11D 7/32; C11D 1/90
[52] U.S. Cl. .................... 252/106; 252/136; 252/142; 252/542; 252/547; 252/DIG. 13; 252/DIG. 14; 424/70
[58] Field of Search ............... 252/136, 142, 542, 547, 252/106, DIG. 13, DIG. 14; 424/70

[56] References Cited

U.S. PATENT DOCUMENTS

| | | | |
|---|---|---|---|
| 3,822,312 | 7/1974 | Sato et al. | 252/527 |
| 3,849,348 | 11/1974 | Hewitt | 252/547 |
| 3,996,146 | 12/1976 | Tarasov | 252/142 |
| 4,148,762 | 4/1979 | Koch et al. | 252/549 |
| 4,246,131 | 1/1981 | Lohr | 252/DIG. 13 |
| 4,321,156 | 3/1982 | Bushman | 252/DIG. 13 |
| 4,374,056 | 2/1983 | Watanabe et al. | 252/546 |
| 4,381,259 | 4/1983 | Homma et al. | 252/542 |

Primary Examiner—John E. Kittle
Assistant Examiner—Mukund J. Shah
Attorney, Agent, or Firm—Richard C. Witte; John V. Gorman; Douglas C. Mohl

[57] ABSTRACT

Shampoo compositions comprising an alkylamido betaine and a quaternary compound and having a pH in the range of from 2 to about 4 are disclosed.

10 Claims, No Drawings

SHAMPOO COMPOSITIONS COMPRISING QUATERNARY IMIDAZOLINIUM COMPOUND AND ALKYLAMIDO BETAINE HAVING LOW PH RANGE

CROSS REFERENCE TO RELATED APPLICATION

This is a continuation of application Ser. No. 735,709, filed on May 17, 1985, abandoned, which is a continuation of application Ser. No. 506,917, filed on June 22, 1983, now abandoned.

BACKGROUND ART

The desire to develop products which simultaneously clean and condition hair has long been present. While the desire has long been present, developing such products has presented in numerable problems. Generally the agents which condition hair best are cationic with one or more long fatty hydrocarbon chains. Hair being negatively charged will allow for the cationic portion to attach to the hair while the long fatty chain(s) provide for ease of combing and hair conditioning.

Cationic materials generally cannot be used with good cleaning anionic surfactants and still deliver good hair condition. This meant that other surfactants such as nonionics, amphoterics and zwitterionics were examined by workers in the field. Many of these efforts are reflected in patents issued in the conditioning shampoo area.

U.S. Pat. No. 3,849,348, Nov. 19, 1974 to Hewitt discloses conditioning shampoos containing betaine, cationic and amine oxide surfactants. U.S. Pat. No. 3,697,452, Oct. 10, 1972 to Olson et al discloses shampoo compositions similar to those in Hewitt. Another patent to Hewitt is U.S. Pat. No. 3,755,559, Aug. 28, 1973 disclosing shampoos containing a tertiary amine oxide, a higher alkyl betaine and a soap. U.S. Pat. No. 3,822,312, July 2, 1974 to Sato discloses shampoos containing a quaternary ammonium salt, a betaine and an additional additive. U.S. Pat. No. 3,990,991, Nov. 9, 1961 to Gerstein discloses shampoos containing amphoteric surfactants and quaternary ammonium compounds. U.S. Pat. No. 4,080,310, Mar. 21, 1978 to Ng et al discloses shampoos containing an amphoteric surfactant, a cationic resin and having a pH as low as 3. U.S. Pat. No. 4,132,679, Jan. 2, 1979 to Tsutsumi et al discloses shampoos containing a phosphoric acid ester salt and a betaine. U.S. Pat. No. 4,231,903, Nov. 4, 1980 to Lindemann et al discloses shampoos containing a mixture of an amido betaine and a phosphobetaine. U.S. Pat. No. 4,247,548, Jan. 27, 1981 to Barker discloses a conditioning shampoo containing a betaine, a polypropoxylated quaternary ammonium chloride surfactant and gum arabic. U.S. Pat. No. 4,294,728, Oct. 13, 1981 to Vanlerberghe et al discloses shampoos containing a cationic, amphoteric or zwitterionic surfactant and a diol. U.S. Pat. No. 4,329,335, May 11, 1981 to Su et al discloses a shampoo composition containing a betaine, an amine oxide and a olymerized quaternary compound. U.S. Pat. No. 4,181,634, Jan. 1, 1980 to Kennedy et al discloses shampoos containing a betaine and a bisquaternary compound.

While the above described references disclose compositions containing components of the type used in the present compositions, they do not teach or suggest totally satisfactory answers to the questions of good cleaning, conditioning and stability (freeze thaw). It is believed that good cleaning with quaternary compounds is in part dependent on limiting the reacting of the quaternary with the fatty acids in sebum.

In addition the references fail to teach or suggest combining betaine surfactants of the type disclosed herein with quaternary ammonium compounds in compositions having a pH in the range of from about 2 to about 4.

It is, therefore, an object of the present invention to provide hair conditioning shampoo compositions which provide good cleaning and conditioning. The good cleaning relates to improved sebum emulsification as well as good lather.

It is a further object of the present invention to provide shampoo compositions containing particular betaine surfactants, and quateernary ammonium compounds and having a pH in the range of from about 2 to about 4.

These and other objects will become more apparent from detailed description which follows.

Unless otherwise indicated, all percentages and ratios herein are by weight.

DISCLOSURE OF THE INVENTION

The compositions of the present invention comprise from about 5% to 70% of an amido betaine, from about 0.5% to about 10% of a quaternary ammonium or imidazolinium compound, from about 20% to about 94.5% water and having a pH in the range of from about 2 to about 4.

DETAILED DESCRIPTION OF THE INVENTION

The essential as well as optional components of the present invention are described in detail below.

Surfactant

The essential surfactants used in the compositions of the present invention are higher alkylamido betaines.

The betaines may be represented by the following structural formula:

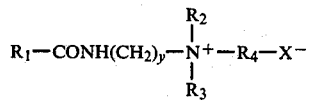

wherein $R_1$ is a long chain alkyl radical having from about 10 to about 18 carbon atoms, $R_2$ and $R_3$ are each alkyl radicals having from about 1 to about 3 carbon atoms, $R_4$ is an alkylene or hydroxy alkylene radical having from about 1 to about 4 carbon atoms, y is an integer from 1 to 4, and X is a carboxylate radical. $R_1$ may be a mixture of long chain alkyl radicals and may contain one or more intermediate linkages or non-functional substituents such as hydroxyl or halogen radicals which do not affect the hydrophobic character of the radical. Examples of betaines useful herein include cocoamidopropyldimethylcarboxymethyl betaine, laurylamidopropyldimethylcarboxymethyl betaine among many others. In many instances the dimethylcarboxymethyl part of the designation is not included.

The amount of surfactant is from about 5% to about 70%, preferably from about 10% to about 25%.

Quaternary Compound

The second essential component of the present invention is a quaternary ammonium or imidazolinium salt.

Quaternary ammonium salts can have the formula:

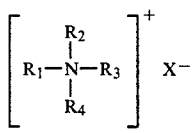

wherein $R_1$ is hydrogen, an aliphatic group of from 1 to 22 carbon atoms, or an aromatic, aryl or alkaryl group having 6 to 20 carbon atoms; $R_2$ is an aliphatic group having from 12 to 22 carbon atoms; $R_2$ and $R_4$ are each alkyl groups having from 1 to 3 carbon atoms; and X is an anion selected from halogen, acetate, phosphate, nitrate and methyl sulfate radicals.

Preferred quaternary ammonium salts are the dialkyl-dimethylammonium chlorides, wherein the alkyl groups have from 12 to 22 carbon atoms and are derived from long chain fatty acids, such as tallow or hydrogenated tallow. The term "tallow" refers to fatty alkyl groups derived from tallow fatty acids. Such fatty acids give rise to quaternary compounds wherein $R_1$ and $R_2$ have predominately from 16 to 18 carbon atoms.

Representative examples of quaternary ammonium salts useful in this invention include ditallowdimethylammonium chloride, ditallowdimethylammonium methyl sulfate, dihexadecyldimethylammonium chloride, di(hydrogenated tallow)dimethylammonium chloride, dioctadecyldimethylammonium chloride, dieicosyldimethylammonium chloride; didocosyldimethylammonium chloride, di(hydrogenated tallow)dimethylammonium acetate, dihexadecyldiethylammonium chloride, dihexadecyldimethylammonium acetate, ditallowdipropylammonium phosphate, ditallowdimethylammonium nitrate, di(coconut-alkyl)dimethylammonium chloride; cetyltrimethylammonium chloride and stearyldimethylbenzylammonium chloride.

Other quaternary ammonium salts useful herein are the compounds of the formula

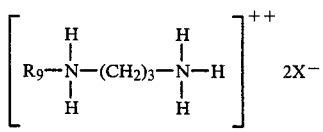

wherein $R_9$ is an aliphatic group having 16 to 22 carbon atoms and X is an anion as above defined. Tallow propanediamine hydrohloride is an example of this quaternary ammonium salt.

Quaternary imidazolinium salts have the formula

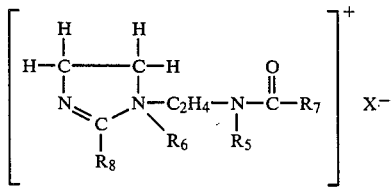

wherein $R_6$ is an alkyl group containing from 1 to 4, preferably from 1 to 2 carbon atoms; $R_5$ is is an alkyl group containing from 1 to 4 carbon atoms or a hydrogen atom; $R_8$ is an alkyl group containing from 1 to 22, preferably at least 15 carbon atoms, or a hydrogen atom; $R_7$ is an alkyl group containing from 8 to 22, preferably at least 15, carbon atoms; and X is an anion, preferably chloride. Other suitable anions include those disclosed with reference to the quaternary ammonium salts described hereinbefore.

Particularly preferred are those imidazolinium salts in which both $R_7$ and $R_8$ are alkyl of from from 12 to 22 carbon atoms, e.g., 1-methyl-1-[(stearoylamide)ethyl]-2-heptadecyl-4,5-dihydroimidazolinium chloride; 1-methyl-1-[(palmitoylamide)ethyl]-2-octadecyl-4,5-dihydroimidazolinium chloride; and 1-methyl-1-[(tallowamide)-ethyl]-2-tallow-imidazolinium methyl sulfate.

The quaternary salt is present at a level of from about 0.5% to about 10%, preferably from about 1% to about 6%.

pH Adjustment

The compositions of the present invention have pH in the range of from about 2 to about 4, preferably from about 2.9 to about 3.8. The compositions are adjusted to this pH range with an acid buffer. The buffering capability is necessary since the pH of the diluted product on hair should be within the range given. Suitable buffer solutions can be prepared, using for example agents such as citric acid, phosphonic acid, phthalic acid, glycine or mixtures thereof. In each case the proper buffering capacity is obtained by adjusting the final pH of the compositions to within the pH range indicated above. This may be done by using a strong acid or a strong base (e.g., HCl or NaOH) as may be needed. The most preferred agent is citric acid. The amount of buffer employed in the present compositions depends on the particular acid chosen but is generally from about 0.3% to about 6%, preferably from about 1% to about 5%.

Water

Water is the last essential component of the present invention and forms the remainder of the composition. It is generally present at a level of from about 20% to about 94.5%, preferably from about 65% to about 80%.

Optional Components

The shampoos herein can contain a variety of nonessential optional components suitable for rendering such compositions more stable and desirable. Such conventional optional ingredients are well known to those skilled in the art, e.g., preservatives such as benzyl alcohol, methyl paraben, propyl paraben and imidazolidinyl urea; betaine surfactants such as lauryl betaine in an amount up to about equal to the amount of the amidobetaine; thickeners and viscosity and modifiers such as a diethanolamide of a long chain fatty acid (e.g., coconut diethanol amide), sodium chloride, sodium sulfate, methylcellulose, polyvinyl alcohol, and ethyl alcohol; suspending agents such as hydrogenated castor oil; opacifiers such as ethylene glycol distearate; perfumes; dyes; and, sequestering agents such as disodium ethylenediamine tetraacetate. Such agents, except for the betaine surfactants, generally are used individually at a level of from about 0.01% to about 10%.

METHOD OF MANUFACTURE

The shampoos of the present invention may be made in a variety of ways. A preferred method is set forth in Example I.

INDUSTRIAL APPLICABILITY

The present compositions are used in a conventional manner for cleaning hair. From about 0.1 g to about 10 g of the composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following composition was prepared and is representative of the present invention (all %'s are on a 100% active basis):

| Component | Wt. % |
| --- | --- |
| Mirataine BB[1] | 18.0 |
| Variquat E228[2] | 4.0 |
| Citric Acid | 4.0 |
| Clindrol Superamide[3] 100 CG | 4.5 |
| Water, perfume, dye and Preservative q.s. | 100.00% |
| pH = 3.1 | |

[1]Lauramidopropyl betaine supplied by Miranol Chemical Company.
[2]Cetrimonium chloride supplied by Sherex Chemical Company.
[3]Cocamide diethanol amide supplied by Clintwood Chemical Company.

Preparation of Example I

The water, betaine and quaternary ammonium compound are mixed together with agitation and heat. Citric acid is then added. When the temperature reaches about 150° F. and cocamide DEA is added and the temperature is increased to the 150° F.–160° F. range. The batch is kept at 150° F.–160° F. until it is clear. The remaining ingredients are then added.

EXAMPLE II

The following is another composition of the present invention:

| Component | Wt. % |
| --- | --- |
| Aerosol 30[1] | 18.0 |
| Variquat E228 | 4.0 |
| Citric Acid | 4.0 |
| Clindrol Superamide 100 CG | 4.0 |
| Water, perfume, dye and Preservative q.s. | 100.00% |
| pH = 2.9 | |

[1]Cocamidopropyl betaine supplied by American Cyanamid.

EXAMPLE III

The following is another composition of the present invention:

| Component | Wt. % |
| --- | --- |
| Mirataine BB | 18.0 |
| Adogen 470 DE[1] | 2.0 |
| Variquat E228 | 2.0 |
| Citric Acid | 4.0 |
| Clindrol Superamide 100 CG | 2.0 |
| Water, perfume, dye and Preservative q.s. | 100.00% |
| pH = 3.1 | |

[1]Ditallowdimonium chloride supplied by Sherex Chemical Company.

EXAMPLE IV

The following composition was prepared and is representative of the present invention (all %'s are on a 100% active basis).

| Component | Wt. % |
| --- | --- |
| Lexaine LM[1] | 18.0 |
| Adogen 470DE | 4.0 |
| Citric Acid | 4.0 |
| Crotein Q[2] | 1.0 |
| Clindrol Superamide 100 CG | 4.0 |
| Ethylene Glycol Distearate | 1.0 |
| Water, perfume, dye and Preservative q.s. | 100.00% |
| pH = 3.0 | |

[1]Lauramidopropyl betaine supplied by Inolex Chemical Company.
[2]Steartrimonium hydrolized animal protein supplied by Croda, Inc.

Preparation of Example

The betaine, citric acid, and quaternary ammonium compound are mixed together with agitation at room temperature. In a separate vessel, the protein compound is dissolved in room temperature water to make a 20% active solution. In a third vessel, amide, water and ethylene glycol distearate are combined and heated to 160° F. All mixtures are agitated until clear solutions are formed. The hot premix is then slowly added to the betaine main mix with high agitation. This crystallizes the ethylene glycol distearate out into small crystals which give the mixture a pearlescent appearance. The protein premix is then added with the remaining ingredients.

EXAMPLE V

To determine the ability of amido betaine/quaternary ammonium compound compositions at pH=3 to emulsify sebum better than the same composition at pH=6, the following study was conducted.

Two aqueous solutions were prepared containing 18% cocamidopropyl betaine and 4% tallowdimonium chloride. One solution was adjsuted to pH=3 while the other had a pH of 6.

These solutions were diluted with distilled water to ⅛ of their original concentration. An aliquot of about 125 grams of each diluted composition was placed at 100° F. for at least two hours. A sample of each diluted composition was also placed at 100° C. until constant weight was obtained.

Artificial sebum, formulated to closely match real sebum, was heated to 100° F. and kept at that temperature. This heated sebum in an amount of 5 grams was added as a top layer to each of the aliquots which were in separatory funnels.

The separatory funnels were then mounted on a platform capable of rotating at 60 rpm. The funnels were rotated for 960 revolutions after which time the solutions were allowed to settle for 2½ minutes. A 30 g. sample of each solution was placed at 100° C. until constant weight was obtained.

The net change in mass per gram of betaine surfactant was determined. For the composition of this invention:

$$\text{Fraction of solids in initial dilution} = \frac{\text{solids content found}}{\text{weight of sample}} =$$

$$\frac{0.57}{16.19} = 0.0352 = Z$$

Fraction of solids which is the betaine surfactant =

(wt. of betaine solution) (fraction betaine)/[(wt. of the betaine solution) (fraction betaine + fraction salt impurity) + (wt.

of quaternary solution) (fraction quaternary) + (amount of acid)] =

$$\frac{600(0.3096)}{600(0.3096 + 0.0466) + (51.0)(.784) + 40} = 0.6325 = Z'$$

Fraction of solids in final composition =

$$\frac{\text{solids content found}}{\text{weight of sample}} = \frac{1.29}{23.16} = 0.0557 = f$$

Net change in mass upon agitation = $\delta$ $Z$(weight of aliquot ($W$)) + $\delta$ = $f$(wt. of aliquot + $\delta$)

$$\delta = \frac{(Z - f)W}{f - 1} = \frac{0.0352 - 0.0057}{0.0557 - 1} (125.53) = 2.7242$$

Net change in mass per gram of betaine surfactant = $y$ $$y = \frac{\delta}{ZWZ'} = \frac{2.7242}{(0.0352)(125.53)(06325)} = 0.97$$

A similar calculation for the pH=6 composition showed that there was only 0.20 grams of change in mass per gram of betaine surfactant.

What is claimed is:

1. A shampoo composition comprising:
   (a) from about 1% to about 2% of a quaternary ammonium compound;
   (b) from about 10% to about 18% of a higher alkylamido betaine; and
   (c) the remainder water;
   wherein the pH of said composition is in the range of from about 2.0 to about 3.4 being maintained within said range by means of a buffering agent.

2. A shampoo composition comprising:
   (a) from about 2% to about 6% of a quaternary ammonium compound;
   (b) from about 14% to about 19% of a higher alkylamido betaine and
   (c) the remainder water;
   wherein the pH of said composition is in the range of from about 2.0 to about 3.4, being maintained within said range by means of a buffering agent.

3. A shampoo composition comprising:
   (a) from about 6% to about 8% of a quaternary ammonium compound;
   (b) from about 19% to about 20% of a higher alkylamido betaine; and
   (c) the remainder water;
   wherein the pH of said composition is in the range of from about 2.0 to about 3.4, being maintained within said range by means of a buffering agent.

4. A shampoo composition according to claim 2 wherein the agent used to maintain a pH of from about 2.0 to about 3.4 is selected from the group consisting of citric acid, phosphoric acid, phthalic acid, glycine, and mixtures thereof.

5. A shampoo composition according to claim 2 wherein the quaternary ammonium compound is a dialkyldimethylammonium salt.

6. A shampoo composition according to claim 5 wherein the higher alkylamido betaine is a higher alkylamidopropyl betaine.

7. A shampoo composition comprising:
   (a) from about 1% to about 3% of a quaternary imidazolinium compound;
   (b) from about 10% to about 18% of a higher alkylamido betaine; and
   (c) the remainder water;
   wherein the pH of said composition is in the range of from about 2.0 to about 3.4, being maintained within said range by means of a buffering agent.

8. A shampoo composition comprising:
   (a) from about 3% to about 7% of a quaternary imidazolinium compound;
   (b) from about 14% to about 19% of a higher alkylamido betaine; and
   (c) the remainder water;
   wherein the pH of said composition is in the range of from about 2.0 to about 3.4, being maintained within said range by means of a buffering agent.

9. A shampoo composition comprising:
   (a) from about 6% to about 8% of a quaternary imidazolinium compound;
   (b) from about 19% to about 20% of a higher alkylamido betaine; and
   (c) the remainder water;
   wherein the pH of said composition is in the range of from about 2.0 to about 3.4, being maintained within said range by means of a buffering agent.

10. A shampoo composition according to claim 7 wherein the higher alkylamido betaine is a higher alkylamidopropyl betaine.

* * * * *